(12) United States Patent
White

(10) Patent No.: US 8,447,671 B1
(45) Date of Patent: May 21, 2013

(54) SYSTEM AND METHOD FOR PROVIDER EVALUATION AND CLAIMANT DIRECTION

(75) Inventor: Jeffrey A. White, Miami, FL (US)

(73) Assignee: Accident Fund Insurance Company of America, Lansing, MI (US)

( * ) Notice: Subject to any disclaimer, the term of this patent is extended or adjusted under 35 U.S.C. 154(b) by 241 days.

(21) Appl. No.: 12/966,259

(22) Filed: Dec. 13, 2010

(51) Int. Cl.
*G06Q 40/00* (2006.01)
(52) U.S. Cl.
USPC .................................. 705/35; 705/4
(58) Field of Classification Search
USPC ............................ 705/2–4, 35–40
See application file for complete search history.

(56) References Cited

U.S. PATENT DOCUMENTS

| | | | |
|---|---|---|---|
| 5,724,379 | A | 3/1998 | Perkins et al. |
| 6,223,164 | B1 | 4/2001 | Seare et al. |
| 2008/0288286 | A1* | 11/2008 | Noreen et al. ............ 705/2 |

* cited by examiner

*Primary Examiner* — Thu Thao Havan
(74) *Attorney, Agent, or Firm* — Dickinson Wright PLLC

(57) ABSTRACT

A method and system for evaluating medical service providers, and before or after an initial medical service provider visit by a claimant, determining whether to direct that claimant on subsequent medical service provider visits to a different medical service provider to optimize efficiency of care and minimize cost at the claim level.

20 Claims, 1 Drawing Sheet

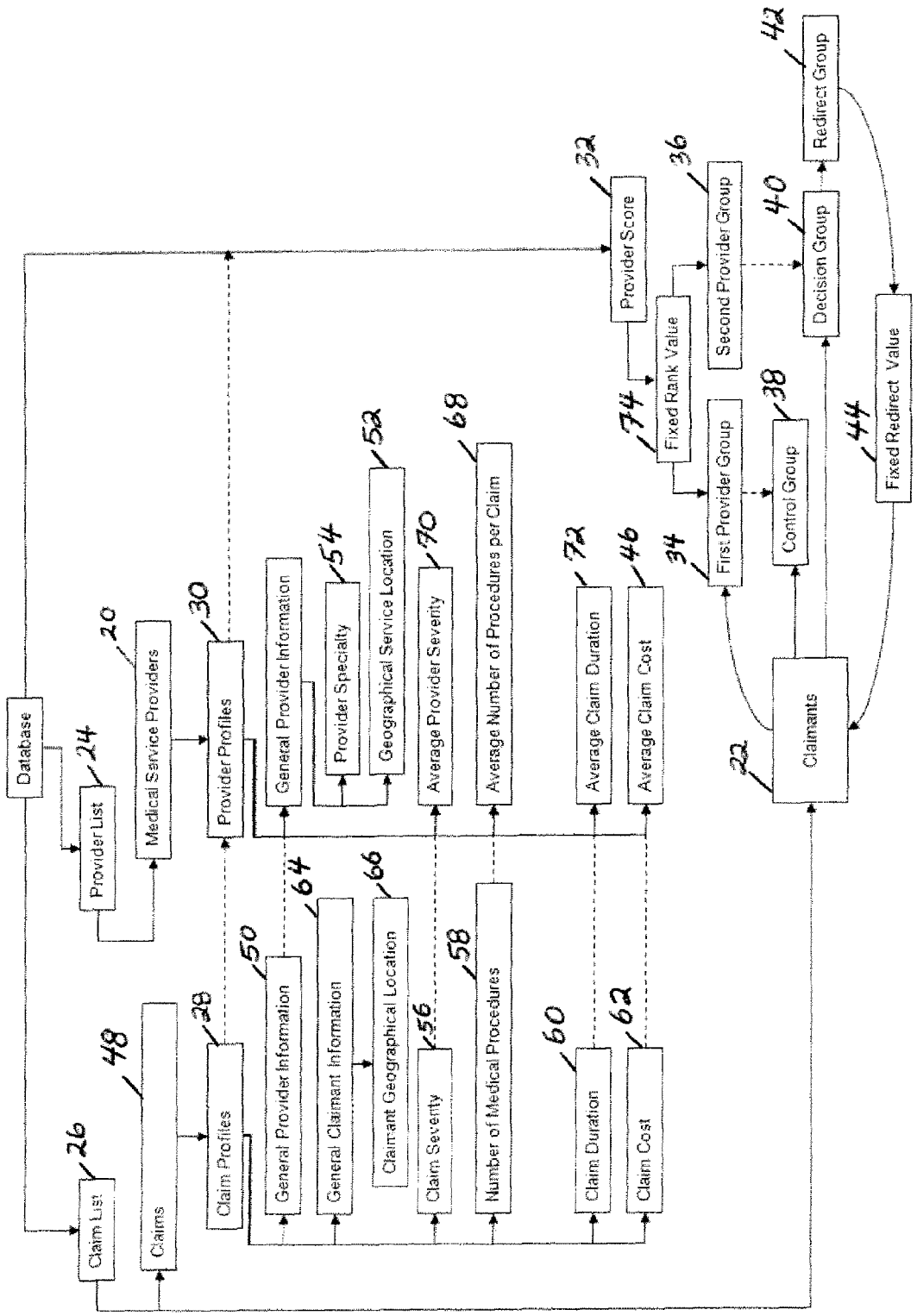

SYSTEM AND METHOD FOR PROVIDER EVALUATION AND CLAIMANT DIRECTION

BACKGROUND OF THE INVENTION

1. Field of the Invention

A system and method of evaluating medical service providers, and before or after an initial medical service provider visit by a claimant, determining whether to direct that claimant on subsequent medical service provider visits to a different medical service provider to optimize efficiency of care and minimize cost at the claim level.

2. Description of the Prior Art

Insurance companies, organizations, and businesses constantly strive to manage health care costs while maintaining or improving patient care. These health care costs include the costs of claims associated with group health, individual health, and property & casualty insurance. In view of increasing health care costs and increasing percentages of a business's or organization's revenue these costs represent, insurance companies, businesses, and organizations are taking steps to introduce new methods of managing claims and reducing costs. One such method includes storing a medical service provider list on a database wherein each medical service provider has at least one provider profile including general provider information. The method may also include storing a claim list including all claimants and claims made by claimants with all of the medical service providers on the provider list. Claim profiles are developed for each claim on the claim list including general provider information and general claimant information.

Prior methods may also assign a provider score for each of the provider profiles based on the claim profiles. These methods may also rank the plurality of medical service providers by the provider scores in that they group the medical service providers achieving provider scores above a fixed rank value into a first provider group and groups the medical service providers achieving provider scores below a fixed rank value into a second provider group. Prior-art medical service provider groups are often tied to provider networks.

Insurance companies, organizations, and businesses typically use provider networks to control medical service costs. In a provider network of medical service providers, fixed rates or standardized discounts apply to given types of medical service. However, provider networks do not limit the number of medical procedures performed for a given claimant during a given claim (utilization), and overall claim costs can be quite steep. A discount or fixed medical service rate as used in a provider network does not truly lead to optimized medical costs at the claim level if utilization is not controlled. Currently, the prior art methods of provider evaluation are limited in their ability to improve efficiency and reduce costs.

In view of the above issues, a method and system is needed to transform the processing of claimants. Without the additional step of directing certain types of claimants to specific medical service providers, not provider networks, the success of directing claimants cannot be effectively measured and used to redefine medical service provider groups and claimant groups in order to improve efficiency and optimize medical costs at the claim level.

SUMMARY OF THE INVENTION

A system and method of evaluating medical service providers, and before or after an initial medical service provider visit by a claimant, determining whether to direct that claimant on subsequent medical service provider visits to a different medical service provider to optimize efficiency of care and minimize cost at the claim level. The system and method can be employed either before or after a claimant visits a medical service provider.

A first advantage of the subject provider evaluation and claimant direction method is the ability to control medical costs both outside traditional provider networks as well as inside provider networks. In the subject method of establishing medical service provider groups and claimant groups, eligible claimants can be directed to the most efficient medical service providers at the claim level. Overall claim cost is greatly influenced by the number of medical procedures for a given claim. In traditional provider networks, the number of medical procedures performed per claim is not optimized, only the cost per procedure type.

A second advantage of the subject method is that the make-up of provider groups and claimant groups can be easily altered in the database by the change of two basic parameters: fixed rank value and fixed redirect value. These changes can be made without moving providers in and out of provider networks, changes that would be visible and potentially frustrating to claimants attempting to select a medical service provider from a list of approved providers.

A third advantage of the subject method is that no provider network incentives are required to control medical costs. Medical service providers are not required to discount their services to be part of a provider network in the subject method. Instead, if a medical service provider performs efficiently at the claim level their provider score will improve and they will be more likely to have additional claimants directed to them. One example of efficient performance would be minimizing the number of medical procedures performed per claim and minimizing claim duration.

The invention provides for a provider evaluation and claimant direction method characterized by grouping claimants making claims to medical service providers in a first provider group into a control group and grouping claimants making claims to medical service providers in a second provider group into a decision group.

The method also includes transforming at least some of the claimants in the decision group into claimants in a redirect group based upon general claimant information. Claimants in the redirect group are directed from medical service providers in the second provider group to medical service providers achieving provider scores above a fixed redirect value in the first provider group.

BRIEF DESCRIPTION OF THE DRAWING

Other advantages of the present invention will be readily appreciated, as the same becomes better understood by reference to the following detailed description when considered in connection with the accompanying drawing wherein:

FIG. 1 is a schematic diagram of the steps performed in the method of provider evaluation and claimant direction in accordance with a preferred embodiment of the present invention.

DETAILED DESCRIPTION OF THE ENABLING EMBODIMENTS

Referring to the FIGURE, wherein like numerals indicate corresponding elements throughout the several views, a system and method of evaluating medical service providers 20 and directing claimants 22 of the type including a computer having a processor, memory, and database is shown in FIG. 1.

In summary, the method includes storing a provider list 24 and claim list 26 on a database. Claim profiles 28 are developed and assigned to provider profiles 30 and also stored on the database. Provider scores 32 are developed for each provider profile 30, and medical service providers 20 are divided into a first provider group 34 and second provider group 36 by provider score 32. Claimants 22 are also grouped into a control group 38 or decision group 40. Some of the claimants 22 in the decision group 40 are transformed into claimants 22 in a redirect group 42. Select claimants 22 in the redirect group 42 are directed to medical service providers 20 achieving provider scores 32 desirable relative to a fixed redirect value 44 in the first provider group 34. The overall effectiveness of the method of provider evaluation and claimant 22 direction is calculated by comparing the average claim cost 46 between the claimant groups 38, 40, 42 and modifying the provider groups 34, 36 and claimant groups 38, 40, 42 based on the difference in average claim cost 46 between the claimant groups 38, 40, 42. The system uses a computer having a processor and memory to perform the method described herein.

A provider list 24 is initially stored on the database. The provider list 24 generally includes a plurality of medical service providers 20 which may have been individually or collectively imported from other databases or added to a created database. Each of the medical service providers 20 in the database will have previously provided services for at least one claim 48, typically an insurance claim, or are added because they provided services for a first claim 48. A provider profile 30, including general provider information 50, is developed for each of the medical service providers 20 on the provider list 24. General provider information 50 in the provider profile 30 preferably includes geographical service location 52 and provider specialty 54. A medical service provider 20 may have more than one provider profile 30 based on having different geographical service locations 52, different provider specialties 54, or both. Of course, the provider profile 30 may be configured to include multiple provider specialties 54 and/or multiple geographical service locations 52 for a medical service provider 20. Additionally, the provider profiles 30 could include any other information desired regarding the medical service providers 20.

A claim list 26 is also initially stored on the database and generally includes claimants 22 and claims 48 made by each claimant 22. The claims 48 and claimants 22 may be added to the claim list 26 individually or collectively from existing sources, or imported to the database, and expanded and added to when new claims 48 occur. In one embodiment the claimants 22 are workers' compensation claimants and the claims 48 are workers' compensation claims. The claimants 22 and claims 48 are linked with the medical service providers 20 on the provider list 24. The claim list 26 generally includes additional details such as claim severity 56 for each claim 48, based on standardized categories of the International Classification of Diseases 9$^{th}$ Edition (ICD9) or derivatives thereof including ICD10 or Diagnosis Related Groupings (DRG), etc. Other additional details may include medical billing details such as the number of medical procedures 58 per claim 48, claim duration 60 based on length of time per claim 48, claim cost 62 based on medical procedure cost and medical service cost per claim 48, or any other information desired to be associated with the claim list 26 may be included.

As the database is created or updated each of the above items of detail may need to be further determined and added to the database. Of course, the database may also include additional details not listed above regarding the medical service providers 20, the claimants 22, or the claims 48. The database may also be configured to be automatically updated with the desired information as a claim 48 is processed.

After the medical service provider 20, claimant 22, and claim 48 details are stored in the database, claim profiles 28 may be developed that include general provider information 50, general claimant information 64, claim severity 56, number of medical procedures 58, claim duration 60, claim cost 62 for each of the claims 48 made by each of the claimants 22, or any other desired information. The general claimant information 64 generally includes claimant geographical location 66 in order to later determine potential geographical service locations 52 convenient for the claimant 22.

The claim profiles 28 are also stored on the database, and each of the claim profiles 28 is assigned to one of the provider profiles 30 based on general provider information 50 or a provider profile 30 is created to go with a new claim profile 28 if the medical service provider 20 was not previously in the database. In other words, the general provider information 50 in each claim 48 will be matched to the provider profile 30 showing the same general provider information 50. Generally, each provider profile 30 would be linked to several claim profiles 28 that give specific details of medical services provided under that provider profile 30. These specific details are used to evaluate the medical service providers 20 as further described below.

Once the claim profiles 28 have been assigned to provider profiles 30, additional details can be added to each of the provider profiles 30 and stored on the database. The additional provider profile 30 details generally include the total number of medical procedures 58 per provider profile 30, an indication of the experience level of a given medical service provider 20. The details also generally include the total number of claims 48 per provider profile 30, another indication of the experience level of a given medical service provider 20, and the average number of procedures per claim 68, calculated by dividing the total number of medical procedures 58 by the total number of claims 48 for a given provider profile 30, which is an indication of efficiency for a given medical service provider 20. The details may also include average provider severity 70, calculated by averaging claim severity 56 per provider profile 30, which is an indication of the types of claims 48 seen by a given medical service provider 20, and the average claim duration 72, calculated by averaging claim duration 60 per provider profile 30, which is another indication of efficiency for a given medical service provider 20. Other details may include the average claim cost 46, calculated by averaging claim cost 62 per provider profile 30, which is another indication of efficiency for a given medical service provider 20. Each of the above details is a measurement of provider performance, reflected by either efficiency or experience of the medical service provider 20. As the database is created or updated each of the above details may need to be further determined and added to the database. Of course, the database may also include additional details not listed above that would be stored with provider profiles 30.

The raw data is transformed by a means such as statistical method or computer calculation into a provider score 32 which is developed for each of the provider profiles 30 by using variables including the average number of procedures per claim 68, average provider severity 70, average claim duration 72, and average claim cost 46 for each provider profile 30. In general, medical service providers 20 who are more efficient and more experienced will have higher provider scores 32. A medical service provider 20 having more than one provider profile 30 will also have more than one provider score 32. Each provider score 32 is stored with the provider profile 30 on the database. The medical service providers 20 are then ranked by the provider scores 32 and medical service providers 20 achieving provider scores 32 on one side of a fixed rank value 74 are grouped into a first provider group 34. The medical service providers 20 achieving provider scores 32 on the other side of the fixed rank value 74 are grouped into a second provider group 36. The persons using the method will choose the fixed rank value 74 as the dividing line between the provider groups 34, 36. The fixed rank value 74 may be predetermined, selected, or calculated based on the provider scores 32.

Once the medical service providers 20 are divided into a first provider group 34 and second provider group 36, claimants 22 making claims 48 to medical service providers 20 in the first provider group 34 are grouped into a control group 38. The claimants 22 in the control group 38 generally remain with the medical service provider 20 they first visit for their claim 48 to receive additional medical services. Claimants 22 making claims 48 to medical service providers 20 in the second provider group 36 are grouped into a decision group 40. The method is characterized by transforming at least some of the claimants 22 in the decision group 40 into claimants 22 in a redirect group 42 based upon general claimant information 64 and claim severity 56. For example, some claimants 22 may not be in a claimant geographical location 66 convenient to a more efficient or experienced medical service provider 20 in the first provider group 34.

Select claimants 22 in the redirect group 42 are directed from medical service providers 20 in the second provider group 36 to medical service providers 20 achieving provider scores 32 desirable relative to the fixed redirect value 44 in the first provider group 34. As with the fixed rank value 74, the persons using the method choose the fixed redirect value 44 to best optimize medical service provider 20 efficiency and experience. Once claimants 22 in the redirect group 42 have been directed to medical service providers 20 in the first provider group 34 achieving provider scores 32 desirable relative to the fixed redirect value 44, the average claim cost 46 is calculated for at least two of the claimant groups 38, 40, 42 including the control group 38, the decision group 40, and the redirect group 42. The overall effectiveness of the method of provider evaluation and claimant 22 direction is calculated by comparing the average claim cost 46 between the claimant groups 38, 40, 42 and modifying the fixed rank value 74 and fixed redirect value 44 based on the difference in average claim cost 46 between the claimant groups 38, 40, 42.

This method is cyclical, similar to the embodiment of a control feedback loop, and intended to improve the average claim cost 46 in all claimant groups 38, 40, 42. Once the fixed rank value 74 and fixed redirect value 44 are modified, medical service providers 20 may be moved between the first provider group 34 and second provider group 36 and claimants 22 may be moved between the control group 38 and decision group 40. Effectiveness of the method will be determined again by comparing the average claim cost 46 between the claimant groups 38, 40, 42, and the fixed rank value 74 and fixed redirect value 44 can be modified again based on the difference in average claim cost 46 between the claimant groups 38, 40, 42.

An advantage of the subject method is that the fixed rank value 74 and fixed redirect value 44 can be modified to improve the average claim cost 46 both inside and outside of traditional provider networks without moving medical service providers 20 in and out of provider networks. Eligible claimants 22 will be directed to the most efficient medical service providers 20 at the claim 48 level, those that optimize the number of medical procedures 58 for a given claim 48. Additionally, efficient medical service providers 20 will not be required to discount their services to achieve desirable provider scores 32, likely a welcome change to the medical service providers 20 over the traditional provider network model.

Obviously, many modifications and variations of the present invention are possible in light of the above teachings and may be practiced otherwise than as specifically described while within the scope of the appended claims. In addition, the reference numerals in the claims are merely for convenience and are not to be read in any way as limiting.

What is claimed is:

1. A method of evaluating medical service providers and directing claimants using a computer and a database comprising the steps of;
   storing a provider list on the database including a plurality of medical service providers;
   developing at least one provider profile including general provider information for each of the medical service providers on the provider list;
   storing a claim list on the database including all claimants and claims made by claimants with all of the medical service providers on the provider list;
   developing claim profiles including general provider information and general claimant information for each of the claims made by each of the claimants;
   executing a profile assignment step in the computer to assign claim profiles to provider profiles based on general provider information;
   executing a provider score step in the computer using predictive analytics to generate a provider score for each of the provider profiles based on the claim profiles in response to executing said profile assignment step;
   executing a sorting step in the computer to rank order the plurality of medical service providers by the provider scores in response to executing said provider score step;
   executing a first provider group step in the computer to programmatically compare the provider scores to a fixed rank value and group the medical service providers having provider scores above the fixed rank value into a first provider group;
   executing a second provider group step in the computer to programmatically compare the provider scores to the fixed rank value and group the medical service providers having provider scores below the fixed rank value into a second provider group;
   executing a control group step in the computer to programmatically group claimants making claims to medical service providers in the first provider group into a control group;
   executing a decision group step in the computer to programmatically group claimants making claims to medical service providers in the second provider group into a decision group;
   executing a redirect group step in the computer to programmatically transform at least some of the claimants in the decision group into claimants in a redirect group in response to processing general claimant information; and
   executing a redirect decision step in the computer to programmatically direct claimants in the redirect group from medical service providers in the second provider group to medical service providers having provider scores at a first pre-determined level relative to a fixed redirect value in the first provider group in response to executing said redirect group step.

2. A method as set forth in claim 1 including determining the average claim cost for at least two of said claimant groups.

3. A method as set forth in claim 2 including determining the effectiveness of the method for provider evaluation and claimant direction by comparing the average claim cost between said claimant groups.

4. A method as set forth in claim 3 including modifying the fixed rank value and fixed redirect value based on the difference in average claim cost between said claimant groups.

5. A method as set forth in claim 4 wherein said claimants are workers' compensation claimants and said claims are workers' compensation claims and said medical service providers have previously provided services for at least one claim.

6. A method as set forth in claim 4 wherein said general provider information includes geographical service location and provider specialty and said general claimant information includes claimant geographical location and claim severity.

7. A method as set forth in claim 6 wherein said claim profiles include number of medical procedures and claim duration and claim cost for each of the claims make by each of the claimants.

8. A method as set forth in claim 7 wherein said claim duration is defined by length of time per claim and said claim cost is defined by medical procedure cost and medical service cost per claim.

9. A method as set forth in claim 7 including determining average number of procedures per claim.

10. A method as set forth in claim 9 wherein said determining average number of procedures per claim is further comprised of determining the total number of medical procedures per provider profile and determining the total number of claims per provider profile and dividing the total number of medical procedures by the total number of claims per provider profile.

11. A method as set forth in claim 9 including storing the claim profiles on the database.

12. A method as set forth in claim 11 wherein said developing a provider score for each of the provider profiles based on the claim profiles includes comparing average number of procedures per claim and average provider severity and average claim duration and average claim cost per provider profile.

13. A method as set forth in claim 12 wherein said average provider severity is defined by averaging claim severity per provider profile and said average claim duration is defined by averaging claim duration per provider profile and said average claim cost is defined by averaging claim cost per provider profile.

14. A method as set forth in claim 12 including storing provider scores and provider profiles on the database.

15. A system for evaluating medical service providers and directing claimants wherein said system comprises
  a computer having a processor and memory;
  a database stored on said computer;
  a provider list stored on said database and including a plurality of medical service providers wherein each of said medical service providers has previously provided services for at least one claim;
  at least one provider profile stored on said database and developed to include general provider information for each of the medical service providers on the provider list wherein said general provider information includes geographical service location and provider specialty;
  a claim list stored on said database including claimants and all claims made by claimants with all of the medical service providers on the provider list;
  a claim severity stored on said database and determined for each claim based on standardized categories;
  a medical procedure number stored on said database and determined from the sum of the claims for a claimant;
  a claim duration stored on said database and based on length of time per claim;
  a claim cost stored on said database and based on medical procedure cost and medical service cost per claim;
  at least one claim profile stored on said database and including general provider information and general claimant information and claim severity and number of medical procedures and claim duration and claim cost for each of the claims made by each of the claimants; and
  wherein general claimant information includes claimant geographical location; and
  wherein the computer system assigns each of the claim profiles to one of said provider profiles in response to processing general provider information; and
  wherein the computer system determines the total number of medical procedures per provider profile, the total number of claims per provider profile, the average number of procedures per claim by dividing the total number of medical procedures by the total number of claims per provider profile, the average provider severity by averaging claim severity per provider profile, the average claim duration by averaging claim duration per provider profile, the average claim cost by averaging claim cost per provider profile, and programmatically develops a provider score for each of the provider profiles by comparing the average number of procedures per claim and average provider severity and average claim duration and average claim cost, and wherein the computer system stores the provider scores and provider profiles on the database, programmatically ranks the plurality of medical service providers by the provider scores, programmatically groups the medical service providers having provider scores that are at a first pre-determined level relative to a fixed rank value into a first provider group, and programmatically groups the medical service providers having provider scores that are at a second pre-determined level relative to a fixed rank value into a second provider group; and
  wherein the computer system programmatically groups the claimants making claims to medical service providers in the first provider group into a control group, groups the claimants making claims to medical service providers in the second provider group into a decision group, transforms at least some of the claimants in the decision group into claimants in a redirect group in response to processing general claimant information and claim severity; and
  wherein the computer system programmatically directs claimants in the redirect group from medical service providers in the second provider group to medical service providers having provider scores at a third pre-determined level relative to a fixed redirect value in the first provider group, determines the average claim cost for at least two of said claimant groups including the control group and the decision group and the redirect group, determines the effectiveness of the method for provider evaluation and claimant direction by comparing the average claim cost between said claimant groups, and modifies the fixed rank value and fixed redirect value in response to the difference in average claim cost between said claimant groups.

16. A system for evaluating medical service providers and directing claimants wherein said system comprises
  a computer having a processor and memory;
  a database stored on said computer;

a provider list stored on said database including a plurality of medical service providers;

at least one provider profile stored on said database and developed to include general provider information for each of the medical service providers on the provider list;

a claim list stored on said database including all claimants and claims made by claimants with all of the medical service providers on the provider list;

at least one claim profile stored on said database and including general provider information and general claimant information for each of the claims made by each of the claimants; and wherein the computer program assigns each of the claim profiles to one of said provider profiles in response to processing general provider information; and wherein the computer system programmatically develops a provider score for each of the provider profiles based on the claim profiles, ranks the plurality of medical service providers by the provider scores, groups the medical service providers having provider scores that are at a first pre-determined level relative to a fixed rank value into a first provider group, groups the medical service providers having provider scores that are at a second pre-determined level relative to a fixed rank value into a second provider group; and wherein the computer system programmatically groups the claimants making claims to medical service providers in the first provider group into a control group, groups the claimants making claims to medical service providers in the second provider group into a decision group, transforms at least some of the claimants in the decision group into claimants in a redirect group based upon general claimant information; and wherein the computer system programmatically directs the claimants in the redirect group from medical service providers in the second provider group to medical service providers having provider scores at a third pre-determined level relative to a fixed redirect value in the first provider group.

17. A system as set forth in claim 16 wherein the computer system determines the average claim cost for at least two of said claimant groups.

18. A system as set forth in claim 17 wherein the computer system determines the effectiveness of the method for provider evaluation and claimant direction by comparing the average claim cost between said claimant groups.

19. A system as set forth in claim 18 wherein the computer system modifies the fixed rank value and fixed redirect value based on the difference in average claim cost between said claimant groups.

20. A system as set forth in claim 19 wherein said claimants are workers' compensation claimants and said claims are workers' compensation claims.

\* \* \* \* \*